United States Patent
Steppe

(10) Patent No.: US 7,523,967 B2
(45) Date of Patent: Apr. 28, 2009

(54) TUBING FITTING

(75) Inventor: Dennis L. Steppe, Corona, CA (US)

(73) Assignee: Alcon, Inc., Hunenberg (CH)

( * ) Notice: Subject to any disclaimer, the term of this patent is extended or adjusted under 35 U.S.C. 154(b) by 454 days.

(21) Appl. No.: 11/259,554

(22) Filed: Oct. 26, 2005

(65) Prior Publication Data

US 2008/0007045 A1    Jan. 10, 2008

Related U.S. Application Data

(60) Provisional application No. 60/635,599, filed on Dec. 13, 2004.

(51) Int. Cl.
F16L 21/00 (2006.01)

(52) U.S. Cl. .............. 285/401; 604/905; 604/533; 604/284

(58) Field of Classification Search ............ 285/401, 285/402, 376; 604/905, 533, 264, 284
See application file for complete search history.

(56) References Cited

U.S. PATENT DOCUMENTS

| | | | | |
|---|---|---|---|---|
| 4,511,359 A * | 4/1985 | Vaillancourt | ............. | 604/411 |
| 4,785,858 A * | 11/1988 | Valentini et al. | ............. | 141/27 |
| 4,810,241 A * | 3/1989 | Rogers | ............. | 604/28 |
| 5,071,413 A * | 12/1991 | Utterberg | ............. | 604/533 |
| 5,125,915 A * | 6/1992 | Berry et al. | ............. | 604/533 |
| 5,201,717 A * | 4/1993 | Wyatt et al. | ............. | 604/192 |
| 5,292,308 A * | 3/1994 | Ryan | ............. | 604/86 |
| 5,425,528 A * | 6/1995 | Rains et al. | ............. | 251/149.1 |
| 5,607,392 A * | 3/1997 | Kanner | ............. | 604/86 |
| 5,609,584 A * | 3/1997 | Gettig et al. | ............. | 604/535 |
| 5,611,785 A * | 3/1997 | Mito et al. | ............. | 604/239 |
| 6,156,025 A * | 12/2000 | Niedospial et al. | ............. | 604/408 |
| 6,183,464 B1 * | 2/2001 | Sharp et al. | ............. | 604/533 |
| 6,562,023 B1 * | 5/2003 | Marrs et al. | ............. | 604/533 |
| 6,955,669 B2 * | 10/2005 | Curutcharry | ............. | 604/533 |
| 7,083,605 B2 * | 8/2006 | Miyahara | ............. | 604/905 |

OTHER PUBLICATIONS

British Standard EN 20594-1:1994 ISO 594-1:1986; "Conical fittings with a 6% (Luer) taper for syringes, needles and certain other medical equipment—Part 1 General Requirements"-Including Amendment A1:1997; 1998; 16 pgs; Brititsh Standards Institution.
British Standard EN 1707:1997; "Conical fittings with a 6% (Luer) taper for syringes, needles and certain other medical equipment—Lock fittings"; 1997; 20 pgs; British Standards Institution.

(Continued)

Primary Examiner—David E Bochna
(74) Attorney, Agent, or Firm—W. David Lee

(57) ABSTRACT

A tubing fitting for use in microsurgery including a female tubing fitting and a male tubing fitting. The female tubing fitting has an external surface with a pair of opposing projections disposed thereon and an internal bore. The male tubing fitting has a second internal bore and a collar at least partially surrounding the second internal bore. The collar has an internal surface with two pairs of opposing sloping ramps disposed thereon. The pairs of opposing sloping ramps are arranged so as to create a pair of opposing spaces for removably receiving the pair of opposing projections.

8 Claims, 2 Drawing Sheets

OTHER PUBLICATIONS

Internet Search Document from Colder Products Company's website; "SMC and SMF1 Series"; Copyright Colder Products 2002-2005; 1 pg.

Internet Search Document from Colder Products Company's website: "Medical Products Overview"; Copyright Colder Products 2002-2005; 6 pgs.

* cited by examiner

TUBING FITTING

This application claims the priority of U.S. Provisional Application No. 60/635,599 filed Dec. 13, 2004.

FILED OF THE INVENTION

The present invention generally pertains to microsurgery and more particularly to tubing fittings for use during ophthalmic surgery.

DESCRIPTION OF THE RELATED ART

A variety of surgical systems are used in ophthalmic surgery. For example, such systems may include a surgical console, accessories (e.g. footswitch, reusable handpieces), and various consumables. The consumables typically include tubing sets that connect to the console and provide a pathway from the console in the non-sterile field to a surgical handpiece or other device that is used in and remains in the sterile field. A tubing fitting is typically used to fluidly couple one end of a piece of tubing to the console, and a second tubing fitting is typically used to fluidly couple another end of the piece of tubing to a surgical device.

Luer fittings are used extensively on medical devices such as syringes, needles, catheters, and tubing sets. Two types are common: luer slip fittings (EN 20594-1, Conical Fittings with a 6% (Luer) Taper for Syringes, Needles and Certain Other Medical Equipment Part 1: General Requirements—Including A1, 1993) and luer lock fittings (EN 1707, Conical Fittings with a 6% (Luer) Taper for Syringes, Needles and Certain Other Medical Equipment—Lock Fittings, 1996). Both types consist of a male fitting and a female fitting. Luer slip fittings are sealably engaged by a friction fit between the male and female luer surfaces. Both the male and female luer slip fittings are colored blue to facilitate identification. Luer lock fittings are sealably engaged with an additional lock feature on the male and female luer surfaces. More specifically, the external female surface includes a pair of opposed flanges proximate its opening. The male fitting includes a collar that receives the female fitting and has a single internal spiral thread that rotationally engages the opposed flanges. Luer lock fittings are typically used in high-pressure applications. Both the male and female luer lock fittings are colored white to facilitate identification.

It should be noted that these fittings are not mutually exclusive. For example, a male luer slip fitting can be engaged with a female luer lock fitting. Similarly, a male luer lock fitting can be engaged with a female luer slip fitting.

Very early in the development of ophthalmic surgery, particularly phacoemulsification, a need arose where it was desirable to prevent the engagement of one type of tubing set used for one purpose (e.g. irrigation) with another type of tubing set used for a second purpose (e.g. aspiration). Therefore, "oversized" luer slip fittings that retained the luer taper but were increased in size were developed. This solution prevented the accidental connection of either a standard luer slip fitting or a standard luer lock fitting and thus promoted patient safety. The male oversized luer slip fitting is colored red and the female oversized luer slip fitting is colored white to facilitate identification.

As time passed and ophthalmic surgical instrumentation grew in sophistication and complexity, the need arose for new fittings that would be physically impossible to connect to standard and/or "oversized" luer fittings. Male and female connectors manufactured by Colder Products Corporation (so-called "CPC connectors") met this need. CPC connectors have a female fitting with a pair of opposing flanges on its external surface proximate its opening, and a male fitting having a collar with a pair of opposing slots for receiving the opposing flanges. The CPC connector is locked or unlocked via a slight rotation of female fitting relative to the male fitting, which frictionally engages the opposing flanges in a pair of opposing notches in the opposing slots. The male CPC fitting is colored white and transparent blue, and the female CPC fitting is colored transparent blue, to facilitate identification.

As ophthalmic surgery continues to increase in sophistication and complexity, the need remains for new tubing fittings that will prevent the accidental misconnection of a standard luer slip fitting, a standard luer lock fitting, an "oversized" luer slip fitting, or a CPC connector.

SUMMARY OF THE INVENTION

One aspect of the present invention is a tubing fitting for use in microsurgery including a female tubing fitting and a male tubing fitting. The female tubing fitting has an external surface with a pair of opposing projections disposed thereon and an internal bore. The male tubing fitting has a second internal bore and a collar at least partially surrounding the second internal bore. The collar has an internal surface with two pairs of opposing sloping ramps disposed thereon. The pairs of opposing sloping ramps are arranged so as to create a pair of opposing spaces for removably receiving the pair of opposing projections. When the pair of opposing projections are disposed in the pair of opposing spaces, the male tubing fitting may be sealingly locked into the female tubing fitting by rotating the collar. The pairs of opposing sloping ramps and the pair of opposing spaces create a geometry that prevent engagement with conventional luer and CPC fittings.

BRIEF DESCRIPTION OF THE DRAWINGS

For a more complete understanding of the present invention, and for further objects and advantages thereof, reference is made to the following description taken in conjunction with the accompanying drawings in which.

DETAILED DESCRIPTION OF THE PREFERRED EMBODIMENTS

Figure 1:
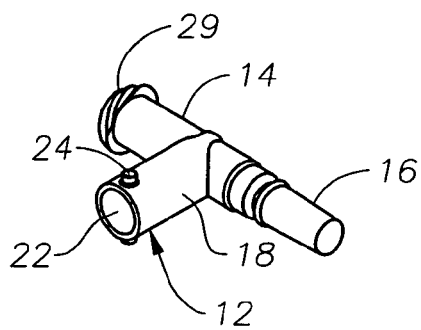
FIG. 1 is a perspective view of a female tubing fitting according to a preferred embodiment of the present invention.
Figure 4:
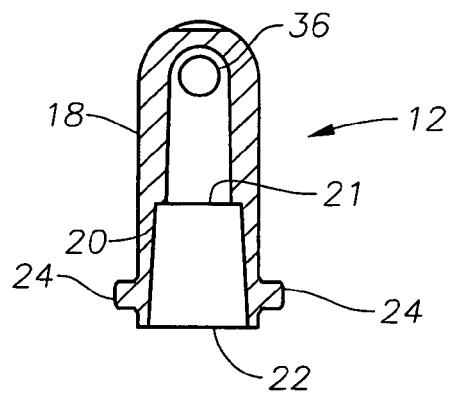
FIG. 4 is a sectional view of the female tubing fitting of FIG. 1 along line 4-4.
Figure 2:
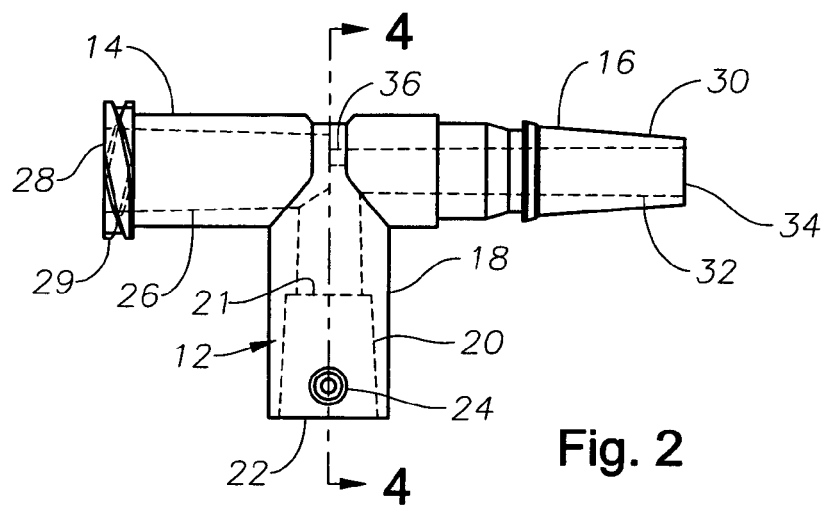
FIG. 2 is a top view of the female tubing fitting of FIG. 1.
Figure 3:
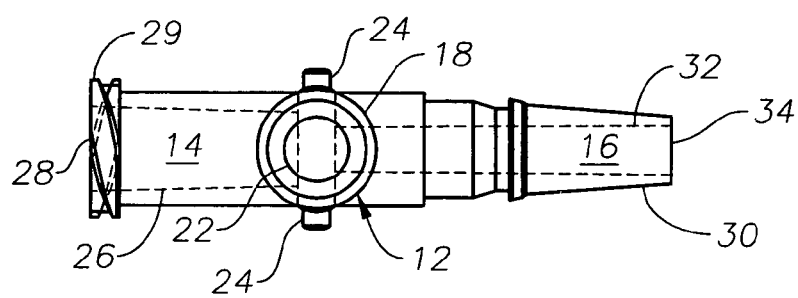
FIG. 3 is a side view of the female tubing fitting of FIG. 1.

The preferred embodiments of the present invention and their advantages are best understood by referring to FIGS. 1 through 7 of the drawings, like numerals being used for like and corresponding parts of the various drawings.

As shown in FIGS. 1-4, female tubing fitting 12 is shown having a "T-connector" configuration. In this configuration, female tubing fitting 12 has a threaded fitting 14 and a male plug 16. Female tubing fitting 12 preferably includes an external surface 18, an internal bore 20 having a luer taper and a shelf 21, and an opening 22. Internal bore 20 is sized so as to prevent engagement with a conventional oversized male luer slip fitting. Shelf 21 prevents engagement with a conventional male luer slip fitting. External surface 18 includes a pair of opposed projections 24. Opposed projections 24 have a geometry and size that prevent engagement with conventional male luer lock and CPC fittings. Threaded fitting 14 preferably has an internal bore 26 having a luer taper, an opening 28, and external threads 29. Male plug 16 preferably has an external surface 30 having a luer taper, an internal bore 32, and an opening 34. Internal bores 20, 26, and 32 are fluidly coupled at a junction 36.

Although not shown in the Figures, female tubing fitting 12 may be formed in a different configuration than a T-connector. For example, threaded fitting 14, male plug 16, and junction 36 may be eliminated and female tubing fitting 12 may terminate in a male plug similar to male plug 16 opposite opening 22 for insertion into the open end of conventional plastic tubing or a standard female luer slip fitting.

Figure 5:
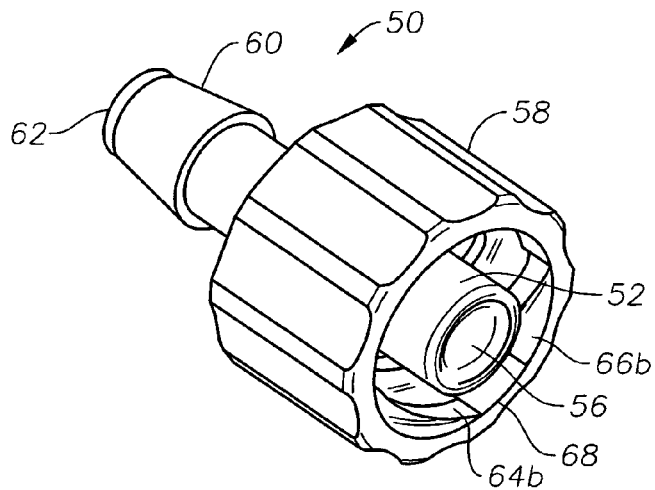
FIG. 5 is a is a perspective view of a male tubing fitting according to a preferred embodiment of the present invention.
Figure 6:
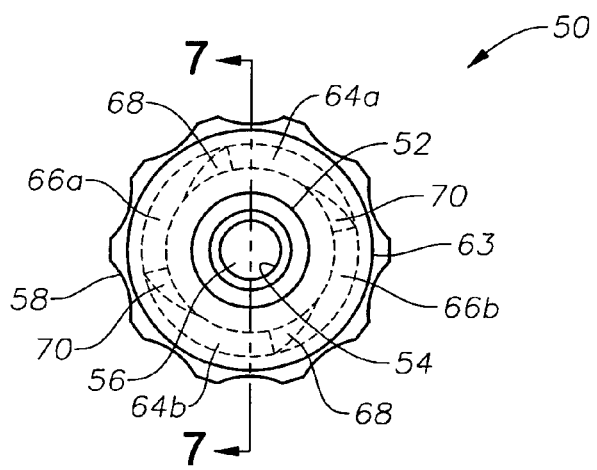
FIG. 6 is front view of the male tubing fitting of FIG. 5.
Figure 7:
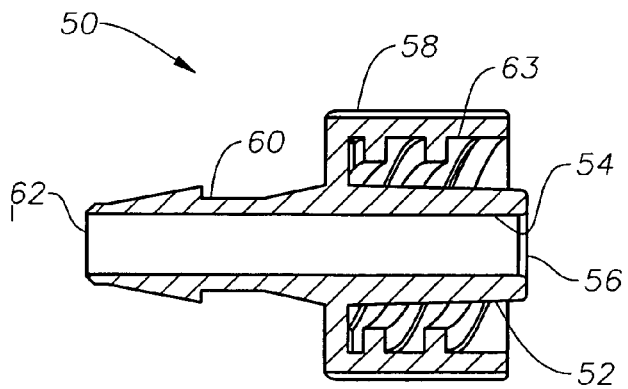
FIG. 7 is a side sectional view of the male tubing fitting of FIG. 5 along line 7-7.

As shown in FIGS. 5-7, male tubing fitting 50 generally includes an external surface 52 having a luer taper, an internal bore 54, an opening 56, a collar 58, a male plug 60, and a second opening 62. Internal bore 20 of female tubing fitting 12 removably receives external surface 52 of male tubing fitting 50. External surface 52 is sized so as to prevent engagement with a conventional female luer slip fitting. Collar 58 has an internal surface 63 with two pairs of opposing sloping ramps 64 and 66. Each ramp 64a and 64b in pair of opposing ramps 64 is sloped in an opposite direction, and each ramp 66a and 66b in pair of opposing ramps 66 is sloped in an opposite direction. Pair of opposing sloping ramps 64 create a pair of opposing spaces 68 for receiving projections 24 of female tubing fitting 12, and pair of opposing sloping ramps 66 create a second pair of opposing spaces 70 for alternatively receiving projections 24. If projections 24 are placed in spaces 68 or 70 and collar 58 is rotated clockwise, male tubing fitting 50 is sealingly engaged with and locked into female tubing fitting 12, and internal bores 20 and 54 are fluidly coupled. Male tubing fitting 50 and female tubing fitting 12 may be unlocked by rotating collar 58 counterclockwise. Pairs of opposing sloping ramps 64 and 66 and pairs of opposing spaces 68 and 70 create a geometry that prevent engagement with the opposing flanges of conventional female luer lock and CPC fittings, and with an oversized female luer slip fitting.

The following describes an exemplary, preferred procedure in which medical personnel may use female tubing fitting 12 and male tubing fitting 50 to fluidly couple a surgical handpiece to a surgical console. Female tubing fitting 12 is fluidly coupled to a connector on a surgical console via threads 29. Female tubing fitting 12 is also fluidly coupled to the first end of a first piece of conventional plastic tubing by inserting male plug 16 into the open end thereof. Male tubing fitting 50 is fluidly coupled to a first end of a second piece of conventional plastic tubing by inserting male plug 60 into the open end thereof. The opposite end of the second piece of plastic tubing is fluidly coupled to a surgical handpiece. The surgical handpiece is then fluidly coupled to the surgical console by inserting projections 24 of female tubing fitting 12 into either spaces 68 or 70 of male tubing fitting 50 and rotating collar 58 clockwise. Such rotation sealingly locks male tubing fitting 50 and female tubing fitting 12. Male tubing fitting 50 and female tubing fitting 12 may be unlocked by rotating collar 58 counterclockwise. The identification of male tubing fitting 50 and female tubing fitting 12 is facilitated by coloring both fittings gray.

From the above, it may be appreciated that the present invention provides improved apparatus and methods for managing and handling the increasingly complex tubing set/surgical device/surgical console connections in ophthalmic surgery. The present invention is illustrated herein by example, and various modifications may be made by a person of ordinary skill in the art. For example, although the tubing fitting of the present invention is described hereinabove in connection with ophthalmic surgery, it may also be used in other microsurgeries, such as, by way of example, otic surgeries or nasal surgeries. In addition, the present invention may be designed so that the male tubing fitting may be locked into the female tubing fitting by rotating the collar in a counterclockwise direction, if desired. Furthermore, the tubing fitting of the present invention may be used to perform other tubing set/surgical device/surgical console connections other than those described above.

It is believed that the operation and construction of the present invention will be apparent from the foregoing description. While the apparatus and methods shown or described above have been characterized as being preferred, various changes and modifications may be made therein without departing from the spirit and scope of the invention as defined in the following claims.

What is claimed is:

1. A tubing fitting for use in microsurgery, comprising:
   a female tubing fitting having an external surface with a pair of opposing projections disposed thereon and an internal bore; and
   a male tubing fitting having a second internal bore and a collar at least partially surrounding said second internal bore, said collar having an internal surface with two pairs of opposing sloping ramps disposed circumferentially along said internal surface, said pairs of opposing sloping ramps being arranged so as to create a pair of opposing spaces for removably receiving said pair of opposing projections,
   wherein when said pair of opposing projections are disposed in said pair of opposing spaces, said male tubing fitting may be sealingly engaged with and locked into said female tubing fitting by rotating said collar.

2. The tubing fitting of claim 1 wherein each of said sloping ramps in each of said pairs of opposing sloping ramps are sloped in an opposite direction.

3. The tubing fitting of claim 1 wherein said internal bore and said second internal bore are fluidly coupled.

4. The tubing fitting of claim 1 wherein said pairs of opposing sloping ramps are arranged so as to create a second pair of opposing spaces for removably receiving said pair of opposing projections.

5. The tubing fitting of claim 4 wherein when said pair of opposing projections are disposed in said second pair of opposing spaces, said male tubing fitting may be sealingly engaged with and locked into said female tubing fitting by rotating said collar.

6. The tubing fitting of claim 5 wherein said internal bore and said second internal bore are fluidly coupled.

7. The tubing fitting of claim 1 wherein said pairs of opposing sloping ramps and said pair of opposing spaces create a geometry that prevent engagement with conventionally sized and shaped luer and CPC fittings.

8. The tubing fitting of claim 1 wherein said tubing fitting is for use in ophthalmic surgery.

* * * * *